(12) United States Patent
Raghavendran et al.

(10) Patent No.: US 8,211,268 B1
(45) Date of Patent: Jul. 3, 2012

(54) TIE LAYER COMPOSITIONS FOR FIBER REINFORCED THERMOPLASTIC—THERMOSET STRUCTURAL ELEMENT

(75) Inventors: Venkatkrishna Raghavendran, Greer, SC (US); Ryan W. Johnson, Moore, SC (US); Pradip Bahukudumbi, Greenville, SC (US); Kirkland W. Vogt, Simpsonville, SC (US)

(73) Assignee: Milliken & Company, Spartanburg, SC (US)

( * ) Notice: Subject to any disclaimer, the term of this patent is extended or adjusted under 35 U.S.C. 154(b) by 207 days.

(21) Appl. No.: 12/661,388

(22) Filed: Mar. 16, 2010

Related U.S. Application Data

(60) Provisional application No. 61/161,936, filed on Mar. 20, 2009.

(51) Int. Cl.
*B32B 27/00* (2006.01)
*B29C 65/00* (2006.01)

(52) U.S. Cl. ................... 156/308.2; 156/307.1

(58) Field of Classification Search .............. 156/163, 156/166, 308.2, 307.1, 307.7, 307.3, 307.5, 156/309.6; 428/364, 365, 375, 105, 108, 428/109, 113, 114, 300.7, 301.4
See application file for complete search history.

(56) References Cited

U.S. PATENT DOCUMENTS

| | | | |
|---|---|---|---|
| 5,074,770 A | 12/1991 | Graefe | 425/117 |
| 5,087,514 A | 2/1992 | Graefe | 428/315.5 |
| 5,264,059 A | 11/1993 | Jacaruso et al. | 156/148 |
| 5,451,451 A * | 9/1995 | Minnick | 442/247 |
| 5,585,155 A | 12/1996 | Heikkila et al. | 428/36.7 |
| 5,643,390 A * | 7/1997 | Don et al. | 156/307.1 |
| 6,056,844 A * | 5/2000 | Guiles et al. | 156/272.4 |
| 7,300,691 B2 | 11/2007 | Callaway et al. | 428/86 |
| 2004/0231790 A1* | 11/2004 | Hou et al. | 156/307.1 |
| 2006/0110599 A1 | 5/2006 | Honma et al. | 428/413 |
| 2007/0071960 A1 | 3/2007 | Eleazer et al. | 428/297.7 |
| 2010/0190398 A1 | 7/2010 | Nair et al. | 442/60 |

FOREIGN PATENT DOCUMENTS

| WO | WO 2008/040506 | 4/2008 |
|---|---|---|
| WO | WO 2008/040509 | 4/2008 |
| WO | WO 2008/040510 | 4/2008 |
| WO | WO 2008/040511 | 4/2008 |

* cited by examiner

*Primary Examiner* — John Goff
(74) *Attorney, Agent, or Firm* — Cheryl J. Brickey

(57) ABSTRACT

A process for simultaneously consolidating to form a fiber reinforced thermoplastic and thermoset structural element that contain, in order; a fiber reinforced thermoplastic member, a tie layer, and a fiber reinforced thermoset member. The fiber reinforced thermoplastic member, contains multiple layers of fibers and a thermoplastic matrix at least partially surrounding the fibers. The fiber reinforced thermoset member contains multiple layers of fibers and a thermoset matrix at least partially surrounding the fibers. The tie layer contains a first polymer and a second polymer.

21 Claims, 5 Drawing Sheets

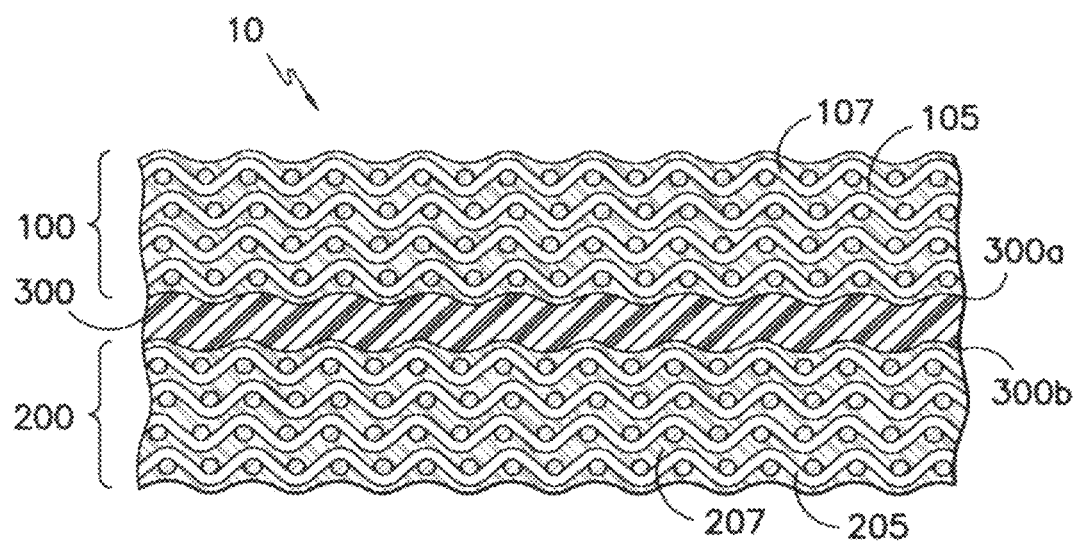
FIG. -1-
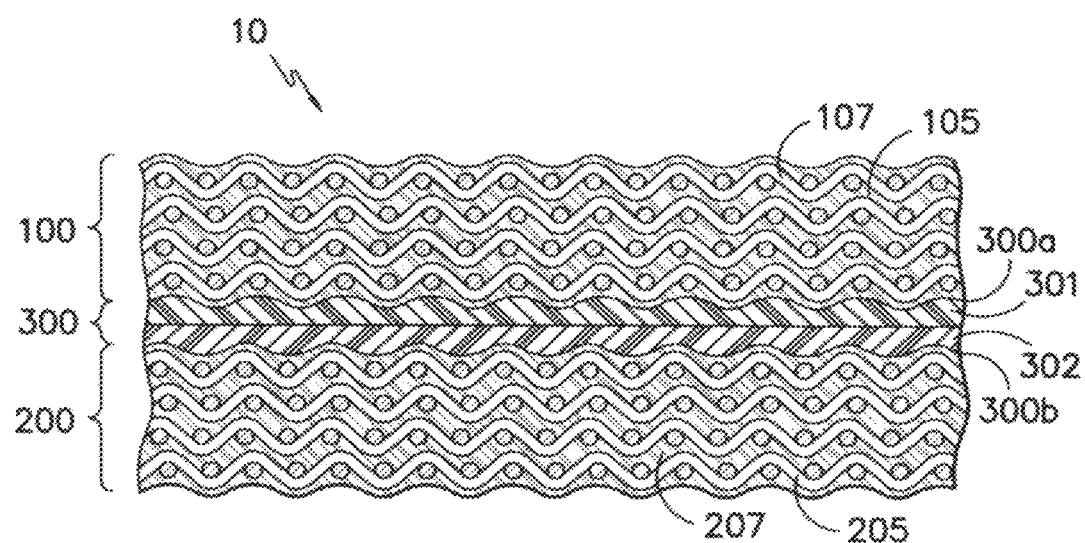
FIG. -2-

US 8,211,268 B1

TIE LAYER COMPOSITIONS FOR FIBER REINFORCED THERMOPLASTIC—THERMOSET STRUCTURAL ELEMENT

CROSS-REFERENCE TO RELATED APPLICATIONS

This application claims priority to Provisional application 61/161,936, filed on Mar. 20, 2009, of which the contents are incorporated by reference in their entirety.

FIELD OF THE INVENTION

The present application is directed to processes for forming fiber reinforced thermoplastic and thermoset structural elements.

BACKGROUND

The goal of bonding the same, similar or totally dissimilar layers of polymeric resin materials to provide a laminate product of reliable and durable performance poses a problem of materials engineering for which a practical and effective solution is often elusive. This is particularly true where a rigid thermoplastic resin layer is to be bonded to a thermoset resin layer. Even after relatively brief periods of service, contact adhesives frequently fail with consequent delamination of the component layers of the laminate article.

There is a need for a tie layer to adhere a fiber reinforced thermoplastic member with a fiber reinforced thermoset member. There is also a need for a tie layer that can be processed at the consolidation processing parameters of the thermoplastic member and the thermoset member.

BRIEF SUMMARY OF THE INVENTION

The invention provides a fiber reinforced thermoplastic and thermoset structural element containing, in order; a fiber reinforced thermoplastic member, a tie layer, and a fiber reinforced thermoset member. The fiber reinforced thermoplastic member, contains multiple layers of fibers and a thermoplastic matrix at least partially surrounding the fibers. The fiber reinforced thermoset member contains multiple layers of fibers and a thermoset matrix at least partially surrounding the fibers. The tie layer contains a first polymer and a second polymer. The first polymer is cohesively or mechanically bonded to the surface of the fiber reinforced thermoplastic member. The second polymer is bonded to a fiber reinforced thermoset member. The process of forming the fiber reinforced thermoplastic and thermoset structural element is also disclosed.

BRIEF DESCRIPTION OF THE DRAWINGS

FIG. 1 is a schematic cross-sectional view of one embodiment of the fiber reinforced thermoplastic and thermoset structural element.

FIG. 2 is a schematic cross-sectional view of one embodiment of the fiber reinforced thermoplastic and thermoset structural element.

DETAILED DESCRIPTION OF THE INVENTION

Figure 3:
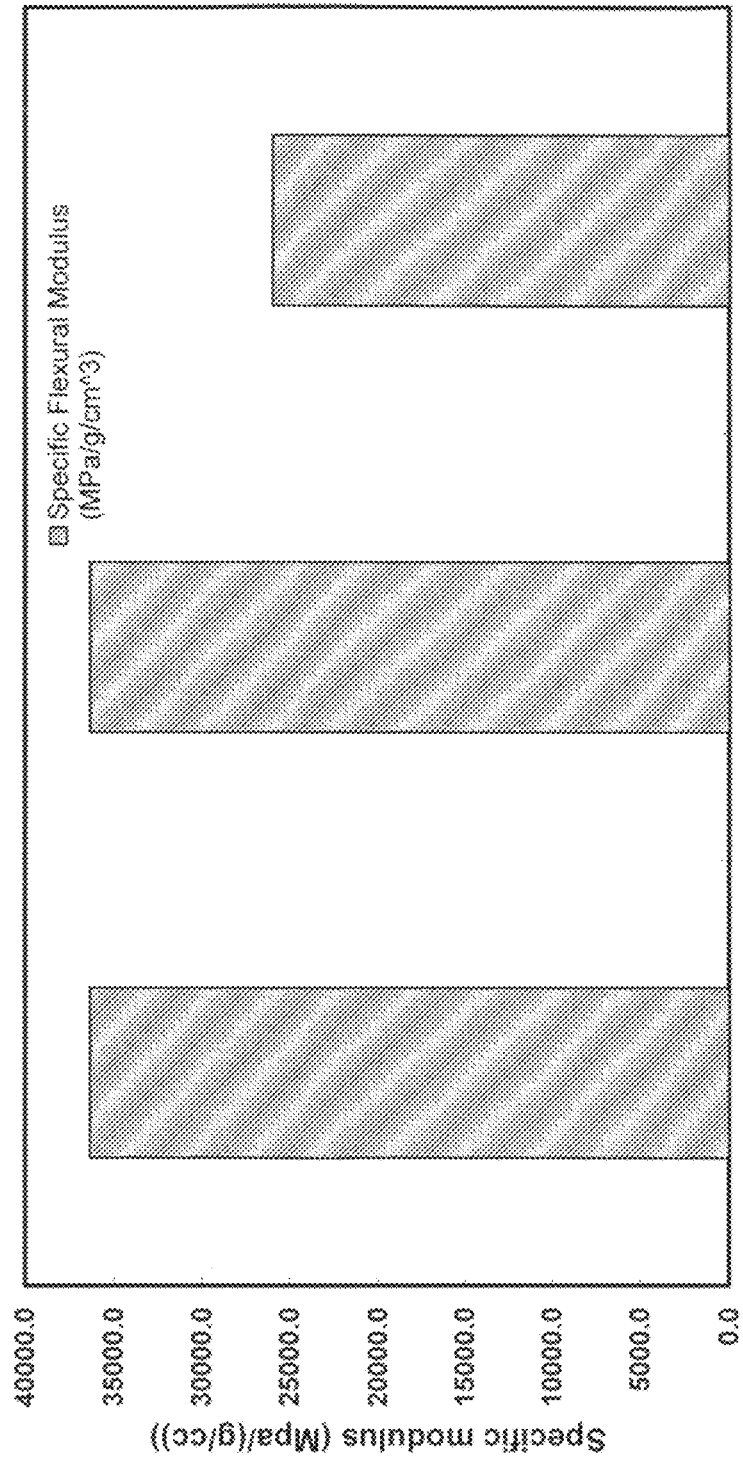
FIG. 3 is a graph showing the specific flexural modulus (MPa/g/cm$^3$) of the examples.

Referring now to FIG. 1, there is shown a fiber reinforced thermoplastic and thermoset structural element 10 containing a fiber reinforced thermoplastic member 100, a tie layer 300, and a fiber reinforced thermoset member 200. The fiber reinforced thermoplastic member 100 contains multiple layers of fibers 105 with a thermoplastic matrix 107. The fiber reinforced thermoset member 200 contains multiple layers of fibers 205 with a thermoset matrix 207. The tie layer 300 attaches the fiber reinforced thermoplastic member 100 and the fiber reinforced thermoset member 200. The tie layer 300 contains a first and a second polymer, the first polymer being compatible with the fiber reinforced thermoplastic member 100 and the second polymer being compatible with the fiber reinforced thermoset member 200. The tie layer 300 has a first surface 300a that includes the first polymer and a second surface 300b that includes the second polymer. The first surface 300a engages the thermoplastic matrix 107 and the second surface 300b engages the thermoset matrix 207.

While the fiber reinforced thermoplastic and thermoset structural element 10 has been depicted in FIG. 1 as including four (4) fiber layers in the fiber reinforced thermoplastic member 100 and four (4) fiber layers in the fiber reinforced thermoset member 200, those of ordinary skill in the art will readily appreciate that the fiber reinforced thermoplastic member 100 can comprise any suitable number of fiber layers in the members 100 and 200. For example, the fiber reinforced thermoplastic member 100 and/or the fiber reinforced thermoset member 200 can comprise two fiber layers, three fiber layers, ten fiber layers, or more.

The fiber reinforced thermoplastic member 100 contains multiple layers of fibers and a thermoplastic matrix. The fiber reinforced thermoset member 200 contains multiple layers of fibers and a thermoset matrix.

The fibers in the fiber layers 105, 205 may be continuous or staple and may have any suitable cross-section including but not limited to circular, elliptical, regular or irregular, tape, rectangular, and multi-lobal.

A non-inclusive listing of suitable fibers for both the fiber reinforced thermoplastic member 100 and the fiber reinforced thermoset member 200 include, fibers made from highly oriented polymers, such as gel-spun ultrahigh molecular weight polyethylene fibers (e.g., SPECTRA® fibers from Honeywell Advanced Fibers of Morristown, N.J. and DYNEEMA® fibers from DSM High Performance Fibers Co. of the Netherlands), melt-spun polyethylene fibers (e.g., CERTRAN® fibers from Celanese Fibers of Charlotte, N.C.), melt-spun nylon fibers (e.g., high tenacity type nylon 6,6 fibers from Invista of Wichita, Kans.), melt-spun polyester fibers (e.g., high tenacity type polyethylene terephthalate fibers from Invista of Wichita, Kans.), and sintered polyethylene fibers (e.g., TENSYLON® fibers from ITS of Charlotte, N.C.). Suitable fibers also include those made from rigid-rod polymers, such as lyotropic rigid-rod polymers, heterocyclic rigid-rod polymers, and thermotropic liquid-crystalline polymers. Suitable fibers made from lyotropic rigid-rod polymers include aramid fibers, such as poly(p-phenyleneterephthalamide) fibers (e.g., KEVLAR® fibers from DuPont of Wilmington, Del. and TWARON® fibers from Teijin of Japan) and fibers made from a 1:1 copolyterephthalamide of 3,4'-diaminodiphenylether and p-phenylenediamine (e.g., TECHNORA® fibers from Teijin of Japan). Suitable fibers made from heterocyclic rigid-rod polymers, such as p-phenylene heterocyclics, include poly(p-phenylene-2,6-benzobisoxazole) fibers (PBO fibers) (e.g., ZYLON® fibers from Toyobo of Japan), poly(p-phenylene-2,6-benzobisthiazole) fibers (PBZT fibers), and poly[2,6-d]imidazo[4,5-b:4',5'-e]pyridinylene-1,4-(2,5-dihydroxy)phenylene] fibers (PIPD fibers) (e.g., M5® fibers from DuPont of Wilmington, Del.). Suitable fibers made from thermotropic liquid-crystalline polymers include poly(6-hydroxy-2-napthoic acid-co-4-hydroxybenzoic acid) fibers (e.g., VECTRAN® fibers from Celanese of Charlotte, N.C.). Suitable fibers also include boron fibers, silicon carbide fibers, alumina fibers, glass fibers, carbon fibers, such as those made from the high temperature pyrolysis of rayon, polyacrylonitrile (e.g., OPF® fibers from Dow of Midland, Mich.), and mesomorphic hydrocarbon tar (e.g., THORNEL® fibers from Cytec of Greenville, S.C.). In certain possibly preferred embodiments, the fibers comprise fibers selected from the group consisting of gel-spun ultrahigh molecular weight polyethylene fibers, melt-spun polyethylene fibers, cellulosic, natural fibers, melt-spun nylon fibers, melt-spun polyester fibers, sintered polyethylene fibers, aramid fibers, PBO fibers, PBZT fibers, PIPD fibers, poly(6-hydroxy-2-napthoic acid-co-4-hydroxybenzoic acid) fibers, carbon fibers, and combinations thereof.

In one embodiment, the fibers are mono axially drawn, thermoplastic fibers. These fibers may be monolayer or multilayer and have any cross-section including tape and core/shell fibers. In one embodiment, the thermoplastic fibers comprise of a base layer of a thermoplastic preferably polypropylene and at least one covering layer of a heat fusible polymer wherein the covering layer is characterized by a softening temperature below that of the base layer to permit fusion bonding upon application of heat. These tapes, fibers, and their textile layer constructions are believed to be more fully described in U.S. Patent Publication No. 2007/0071960 (Eleazer et al.) which is incorporated by reference. In one embodiment, the covering layer of the multilayer fibers contains a high modulus, high viscosity polyolefin majority component and a low molecular weight, low viscosity polyolefin plastomer as a minority component. The high modulus, high viscosity component would provide the strength for reinforcement. The low molecular weight, low viscosity plastomer would reduce the viscosity of the mixture with little or no change to the modulus and improve the toughness by inducing co-crystallization with the majority component. The drop in viscosity would enable the composite fabrics to be processed at lower temperatures (250 F) and pressures approaching vacuum bag conditions. This plastomer allows for consolidation at lower temperatures and/or pressures. More details about the low molecular weight, low viscosity additives and methods of applying the additives may be found in U.S. patent application Ser. No. 12/360,553 (Nair et al.) the contents of which are incorporated by reference. In the embodiment where the fibers are multi-layer, once consolidated, the core of the fibers may be considered the fiber and the covering layer melts and at least partially encapsulates the cores of the fibers and adheres the fibers together forming the matrix. In one embodiment of the invention, the tie layer 300 may adhere to the fibers 105 of the thermoplastic member 100. In some embodiments, the thermoplastic member 100 may only have fibers 105 with no matrix 107.

The fibers may be in any suitable construction in the fiber layers 105, 205 within the fiber reinforced thermoplastic member 100 and the fiber reinforced thermoset member 200. The fiber layers 105, 205 may have a woven, knit, nonwoven (e.g., a needle-punched nonwoven, etc), or unidirectional construction.

For the embodiment where the fiber layers 105, 205 are in a woven construction, the woven layer preferably includes a multiplicity of warp and weft elements interwoven together such that a given weft element extends in a predefined crossing pattern above and below the warp element. One preferred weave is the plain weave where each weft element passes over a warp element and thereafter passes under the adjacent warp element in a repeating manner across the full width of the textile layer. Thus, the terms "woven" and "interwoven" are meant to include any construction incorporating interengaging formation of fibers or yarns.

As will be understood by those of ordinary skill in the art, the fiber layers 105, 205 in the members 100, 200 can be independently provided in each of the aforementioned suitable constructions. For example, the fiber reinforced thermoplastic member 100 may have five (5) fiber layers 105 in a knit construction and five (5) fiber layers 105 in a woven construction. The different constructions may be grouped together, arranged in a repeating pattern or arranged randomly. The thermoplastic matrix 107 of the fiber reinforced thermoplastic member 100 may be any suitable thermoplastic polymer including but not limited to polyolefins such as polypropylene and polyethylene, polyurethane, polyamide, polysulfones, polyketones, polybutylene terephthalate, polycarbonate, poly lactic acid, polyester, and mixtures and co-polymers thereof. Preferably, the thermoplastic matrix 107 is a polyolefin. The polyolefin of the matrix may be a homopolymer, random copolymer, block copolymer or combinations thereof. Some examples of polyolefin polymers that may be used include polypropylene and polyethylene. In one embodiment, the thermoplastic matrix comprises an "A" polymer and a "B" polymer, wherein the A polymer contains a polymer having at least 70% $\alpha$-olefin units and is characterized by a melting temperature lower than the melting temperature of the exterior surface portion of the fibers, and the B polymer contains a co-polymer having at least 50% $\alpha$-olefin units and is characterized by a number-average molecular weight of about 7,000 g/mol to 50,000 g/mol, a viscosity of between about 2,500 and 150,000 cP measured at 170° C., and a viscosity not greater than 10% of the viscosity of the A polymer measured at 170° C.

The thermoset matrix 207 of the fiber reinforced thermoset member 200 comprises a thermoset polymer. The thermoset polymer can be one or more epoxy-based resin, polyester-based resin, phenolics, polyurethanes, vinyl-ester based resin, phenolic-based resin, and the like, preferably an epoxy resin. The thermoset polymer is typically subjected to heat and pressure to cure (chemically react) the resin. The cure is preferably slow at room temperature to prevent reactions that reduce tack, drape and shelf-life, but sufficiently rapid at elevated temperatures to permit reasonably short cure times. Additives can be used to change the viscosity of the uncured resin and to toughen the matrix to reduce brittleness. The epoxide or other reactive group can react chemically with other molecules to form a highly cross-linked three-dimensional network. This chemical reaction transforms the liquid resin into a structural load-bearing solid. The commonly used curing agents for epoxy systems for pre-preg systems are 4,4'-diaminodiphenylsulfone and dicyandiamide, although other amines, anhydrides, acids and many others can be used. When the thermoset matrix 207 is processed, the matrix 207 binds the fibers in the fiber layers 205 together maintaining the orientation and spatial position as it cures, by virtue of its cohesive and adhesive characteristics, and allows for efficient load transfer to and between the fibers.

The tie layer 300 is used to bond the fiber reinforced thermoplastic member 100 and the fiber reinforced thermoset member 200. In some embodiments, the tie layer 300 allows the fiber reinforced thermoplastic member 100 and the fiber reinforced thermoset member 200 to be co-processable at elevated temperatures. In one embodiment, the tie layer 300 in this invention forms a chemical bond with the fiber reinforced thermoset member 200 and a thermobond (mechanical bond) with the fiber reinforced thermoplastic member 100. The thermobond between the tie layer 300 and the thermoplastic matrix 107 is due to the physical interlocking of polymer chains. On a microscopic scale, it is due to chain entanglement which is a function of the radius of gyration, molecular weight, and chain length of the polymers and the ability of the different polymers to crystallize.

In one embodiment, the bond strength between the tie layer 300 and the thermoplastic member 100 needs to be at least 50% of the bond strength between adjacent layers within the thermoplastic member. More preferably, the strength ratio needs to approach 100% or more of the strength of the interlaminar strength between layers of the thermoplastic member.

The first polymer is compatible with the thermoplastic matrix 107. Preferably, the first polymer is a polyolefin. In one embodiment, the first polymer is of the same class of polymer as the thermoplastic matrix.

In one embodiment, the first polymer of the tie layer 300 comprises the same repeating unit as the thermoplastic matrix 107 of the fiber reinforced thermoplastic member 100. In this embodiment, if the thermoplastic matrix 107 is a polypropylene, the first polymer would also contain propylene repeating units. In some embodiments, the second polymer is able to be chemically reacted to the thermoset matrix 207 of the fiber reinforced thermoset member 200. The second polymer may include polyamide (PA), thermoplastic urethane (TPU), and polyester (PET).

layers is contemplated. Some examples of first polymer/second polymer combinations include: PO/PA, PO/TPU, and PO/PET.

The tie layer may be applied to the fiber reinforced thermoplastic and thermoset structural element 10 by any known method including forming a freestanding film by film extrusion or melt-blown film extrusion (or co-extrusion) then applying the free standing film to the members 100, 200 or may be applied to the members 100, 200 by solvent casting, printing, solvent coating, or powder coating. The tie layer may be continuous or discontinuous. In the case where the tie layer is an extruded monolayer or multilayer film, the film may first have multiple slits cut in it to allow the film to be more drapable and facilitates easy lay-up in a mold. One preferred tie layer 300 is a polypropylene/polyamide multi-layered film consisting of a polyamide adhesive on one side and a modified polyolefin on the other side. These films may have different weight percentages of the first and second polymer, for example 75% wt first polymer with 25% wt second polymer or a 50/50 blend by weight of the first and second polymer with an optional compatibilized blend of the first polymer and the second polymer between the two polymers to provide good bonding.

While not being bound to any theory, it is believed that the tie layer 300 and the thermoset matrix 200 in some embodiments chemically bond together. There may also be only mechanical bonding or a mixture of mechanical and chemical bonding between the thermoset matrix 200 and the tie layer 300. The mechanism for the reaction between the second polymer of the tie layer 300 and the fiber reinforced thermoset member 200 for the embodiment where the thermoset matrix 207 is an epoxy and the second polymer of the tie layer 300 is a polyamide is as follows:

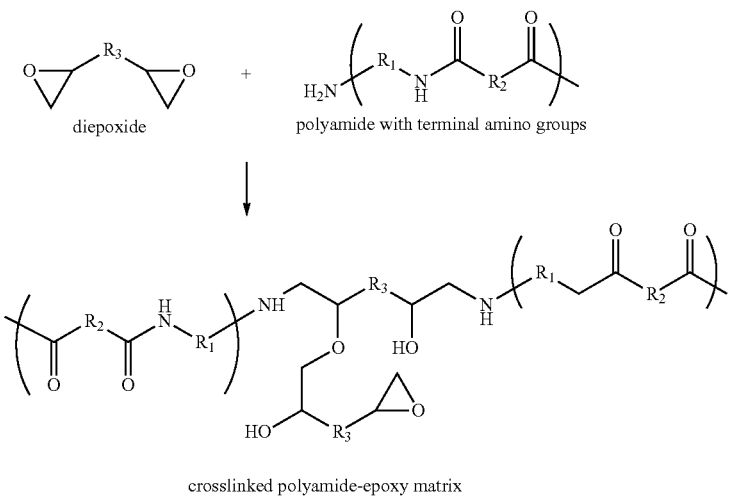

The tie layer 300 may be a single layer of a mixture of the first and second polymer, a co-polymer containing the first polymer and the second polymer, or a multilayered film having a sub-layer 301 containing the first polymer and a sub-layer 302 containing the second polymer such as shown in FIG. 2. The sub-layers are oriented such that the first sub-layer 301 is adjacent the fiber reinforced thermoplastic member 100 and the second sub-layer is adjacent the fiber reinforced thermoset member 200. While the tie layer 300 is shown in FIG. 2 having two sublayers, any number of sub- The chemistry of epoxies is based primarily on the high reactivity of the strained three-membered oxirane ring. The oxirane ring opens up when attacked by a suitable nucleophile and polymerization takes place. The amino groups, both primary and secondary types, in the polyamide structure are sufficiently nucleophilic; the amide groups are not. The free amino groups provide the reactive sites for cross-linking epoxy resin chains. The reaction is accelerated at elevated temperatures where the curing of the epoxy resins is carried out. The melting of the polyamide and additional mobility of the polymer chains at those temperatures will further facilitate the amino groups in the polyamide to orient towards the epoxy resin and facilitate the formation of a co-cured thermoset thermoplastic resin bond.

The use of the tie layer of the invention allows for the consolidation of the fiber reinforced thermoplastic and thermoset structural element 10 simultaneously meaning that the fiber reinforced thermoplastic member 100, the tie layer 300, and the fiber reinforced thermoset member 200 are all heated together with optional pressure (before heating the fiber layers 105 and 205 within the members 100 and 200 are not adhered to one another).

In one embodiment, the process of forming a fiber reinforced thermoplastic and thermoset structural element comprises:

a) providing a fiber reinforced thermoplastic member, where the fiber reinforced thermoplastic member comprises multiple layers of fibers and a thermoplastic matrix at least partially surrounding the fibers, where the multiple layers of fibers may be attached or unattached from one another;

b) providing a fiber reinforced thermoset member, where the fiber reinforced thermoset member comprises multiple layers of fibers and a thermoset matrix at least partially surrounding the fibers, where the multiple layers of fibers may be attached or unattached from one another;

c) applying a tie layer between the fiber reinforced thermoplastic member and the fiber reinforced thermoset member, where the tie layer comprises a first polymer and a second polymer;

d) consolidate the fiber reinforced thermoplastic member, the tie layer, and the fiber reinforced thermoset member simultaneously under heat and optionally pressure to form the fiber reinforced thermoplastic and thermoset structural element;

Consolidation may be conducted at any suitable temperature and pressure conditions to facilitate both the bonding within the members 100 and 200 and the bonding between members 100 and 200 through the tie layer 300. Heated batch or platen presses may be used for multi-layer consolidation. In one exemplary practice, autoclaves or vacuum bags may be used to provide the pressure during consolidation. Continuous consolidation methods such as calendaring or use of a single or double belt laminator may likewise be employed. It is contemplated that any other suitable press may likewise be used to provide appropriate combinations of temperature, pressure, and residence time. According to a potentially preferred practice, heating is carried out at a temperature of about 250-370° F. and a pressure of greater than 10 psi, preferably about 15-300 psi.

After consolidation the thermoplastic matrix of the fiber reinforced thermoplastic member adheres at least a portion of the fibers of the fiber reinforced thermoplastic member together and the thermoset matrix of the fiber reinforced thermoset member adheres at least a portion of the fibers of the fiber reinforced thermoset member together. The first polymer of the tie layer is thermobonded to the surface of the fiber reinforced thermoplastic member; and the second polymer of the tie layer is bonded to the surface of the fiber reinforced thermoset member.

The fiber reinforced thermoplastic and thermoset structural element 10 may also be formed by consolidating the fiber reinforced thermoplastic member 100 and the tie layer 300 together under the fiber reinforced thermoplastic member 100 consolidation conditions, then adding the fiber reinforced thermoset member 200 and consolidating the whole fiber reinforced thermoplastic and thermoset structural element 10 at the consolidation conditions of the fiber reinforced thermoset member 200.

In another embodiment, the fiber reinforced thermoplastic and thermoset structural element 10 may also be formed by consolidating the fiber reinforced thermoset member 200 and the tie layer 300 together under the fiber reinforced thermoset member 200 consolidation conditions, then adding the fiber reinforced thermoplastic member 100 and consolidating the whole fiber reinforced thermoplastic and thermoset structural element 10 at the consolidation conditions of the fiber reinforced thermoplastic member 100.

EXAMPLES

Various embodiments of the invention are shown by way of the Examples below, but the scope of the invention is not limited by the specific Examples provided herein.

Three-Point Flexural Testing of Composite Samples (ASTM D790)

The three point flexural tests were conducted in accord with ASTM D 790 using the MTS mechanical testing machine. The modulus of elasticity in bending, strength and toughness were calculated from the measured flexural stress-strain response of the composite material. The ASTM D 790 test method covers the determination of flexural properties of un-reinforced and reinforced plastics, including high-modulus composites and electrical insulation materials in the form of rectangular bars molded directly or cut from sheets, plates or molded shapes. The test procedure used is detailed below:

1) Cut samples (3"×8") using a high pressure water jet.

2) Condition the samples at 23±2° C. and 50±5% relative humidity for at least 40 hours prior to testing. Conduct the test under the same temperature and humidity conditions.

3) Measure the thickness of the samples using a micrometer with a clutch or a vernier caliper.

4) Set up the MTS mechanical testing machine for flexural testing. The test samples of rectangular cross section rest on two supports and are loaded by means of a loading nose midway between the supports. The loading nose and supports have cylindrical surface geometries to avoid excessive indentation, or failure due to stress concentration directly under the loading nose.

a) Set support span at 152 mm (6 inches)

b) Align the loading nose and supports so that the axes of the cylindrical surfaces are parallel and the loading nose is midway between the supports. Center the test specimen on the supports, with the long axis of the specimen perpendicular to the loading nose.

c) Set the machine for a rate of crosshead speed of 10 mm/min.

d) Calibrate the load cell. Error in the load measuring system should not exceed ±1%.

e) Apply the load to the test specimen at the specified crosshead rate, and record simultaneous load-deflection data. The deflection is measured from the motion of the loading nose relative to the supports. Load-deflection curves are then plotted to determine the tangent modulus of elasticity, flexural strength, and the total work as measured by the area under the load-deflection curve.

When a homogeneous elastic material is tested in bending as a simple beam supported at two points and loaded at the midpoint, the maximum stress in the outer surface of the test specimen occurs at the midpoint. This stress can be calculated for any point on the load-deflection curve by using the following equation:

$$\sigma_f = 3PL/2bd^2$$

where:
   $\sigma_f$=stress in the outer fibers at midpoint, MPa
   P=load at a given point on the load-deflection curve, N
   L=support span, mm
   b=width of the test specimen
   d=thickness of the test specimen The flexural strength is the maximum flexural stress sustained by the test specimen during the bending test. This can be calculated by setting P in the above equation to the peak load measured from the load-displacement curve.

The flexural strain, $\epsilon_f$, is the nominal fractional change in the length of an element on the outer surface of the test specimen at mid-span, where maximum strain occurs. It can be calculated for any given displacement using the following equation:

$$\epsilon_f = 6Dd/L^2$$

where:
   $\epsilon_f$=strain in the outer surface, mm/min
   D=maximum deflection of the center of the beam, mm The tangent modulus of elasticity, often referred to as the modulus of elasticity, is then given by the ratio, within the limit of elasticity, of stress to corresponding strain. It is calculated by drawing a tangent to the steepest initial straight-line portion of the load-deflection curve and using the equation given below.

$$E_B = L^3 m/4bd^3$$

where:
   $E_B$=modulus of elasticity in bending, MPa
   m=slope of the tangent to the initial straight-line portion of the load deflection curve, N/mm Multiaxial Impact Testing (ASTM D3763)

The most commonly used impact tests, such as the Izod test or the Gardner Impact test, measure only one quantity—the total energy absorbed by the specimen during the impact event. The failure of composites is complex and progressive and not always catastrophic. The point of interest during an impact event will depend on the performance criterion from the functional requirement statement for a given application. The controlling variable may be deflection, force, energy and the failure limit. The multi-axial instrumented impact test (ASTM D3763) allows us to study the complete spectrum of composite failure mechanisms from incipient damage up to through-penetration. The critical parameters determined for comparing the impact response of different composite constructions were, 1) load/energy absorbed at incipient damage, 2) maximum load/energy to maximum load, 3) deflection to maximum load and 4) total energy absorbed for through penetration.

Fiber Layers for the Fiber Reinforced Thermoplastic Member

Woven fibrous layers were formed from tape fibers in a 2×2 twill weave with 11 ends/inch and 11 picks/inch. The tape fibers had a size of 1020 denier per fiber, a width of 2.2 mm, and a thickness of 65 μm. The tape fibers had a polypropylene core having a tensile modulus of about 19 GPa surrounded by two first layers. The first layers contained a propylene copolymer having Mw of 280,000 g/mol, vicat softening point of 107° C., a melting temperature of about 117° C., and viscosity of 5,700,000 cP at 170° C. and Licocene® 2602. Licocene® 2602 is a metallocene type of propylene-ethylene co-polymer obtained from Clariant. The tape fibers were 14% by weight Licocene®. The first layers comprised about 15% by thickness of the total tape fiber.

Fiber Layers for the Fiber Reinforced Thermoset Member

Woven layers were formed from woven carbon fibers in an epoxy pre-preg made by Advanced Composite Group. The resin was ACG Component Prepreg MTM28. The woven fabric was a 4×4 twill weave fabric using T300 carbon fiber (3K tow size) and each layer of fabric had a weight of about 280 gm/m². The prepreg is specified to contain 42% epoxy resin by weight.

Tie Layer

The tie layer used between the thermoplastic member and the thermoset members was Nolax® 45.311 (40 gsm) PP/PA film available from Nolax. The film contained a 30 gsm layer of polypropylene and a 10 gsm layer of polyamide. The tie layer was oriented such that the PP faced the thermoplastic member and the polyamide faced the thermoset member.

Samples were created by sandwiching a number of fiber layers of the fiber reinforced thermoplastic member between a number of fiber layers of the fiber reinforced thermoset member on either side of the thermoplastic member. In the Invention Examples 2 and 3, a tie layer was used between the members. The samples were consolidated at 250° F. and 90 psi for a time of 90 minutes. The constructions of the examples are summarized in Table 1.

TABLE 1

Construction of Examples

| Sample ID | Thermoplastic member | Thermoset member (on both sides of the thermoplastic member) | Tie layer |
| --- | --- | --- | --- |
| Control Ex. 1 | None | 9 layers | None |
| Invention Ex. 2 | 10 layers | 2 layers | Yes |
| Invention Ex. 3 | 15 layers | 1 layer | Yes |

The samples were tested using the Three-point flexural testing of composite samples (ASTM D790) as described above. The elastic modulus per mass density of the material, also known as the specific modulus is calculated and reported for each sample. The specific modulus of the composite samples tested is reported in FIG. 3. The raw data is summarized below in Table 2.

TABLE 2

Three-point flexural testing results

| Sample ID | Thickness (mm) | Weight (g) for 3" × 8" sample | Flex Mod (MPa) | Stiffness (N/mm) | Peak Load (N) |
| --- | --- | --- | --- | --- | --- |
| Control Ex. 1 | 2.90 | 65.03 | 52553 | 111.60 | 2404.65 |
| Invention Ex. 2 | 2.86 | 47.47 | 38892 | 78.99 | 1235.58 |
| Invention Ex. 3 | 2.93 | 41.55 | 23823 | 51.72 | 469.84 |

Three point bend tests (ASTM D790) of the samples outlined below reveal significant differences in performance related to the various ratios of thermoset members 200 to thermoplastic member 100 within the structure. The overall bending performance of the structures in the linear elastic region is consistent with sandwich panel theories. These theories explain the elastic bending of the structure through knowledge of the constituent material properties. Usually, the dominant properties include the tensile modulus of the outer thermoset members, the tensile modulus of the thermoplastic member, and the shear modulus of the thermoplastic layer.

The relative influence of these properties is driven by the geometric arrangement of the materials.

The notable difference in the strength of the structures compared herein is dictated by the weakest link within the structure. Analysis of a sandwich structure in bending must account for all potential failure modes of the structure.

Figure 4:
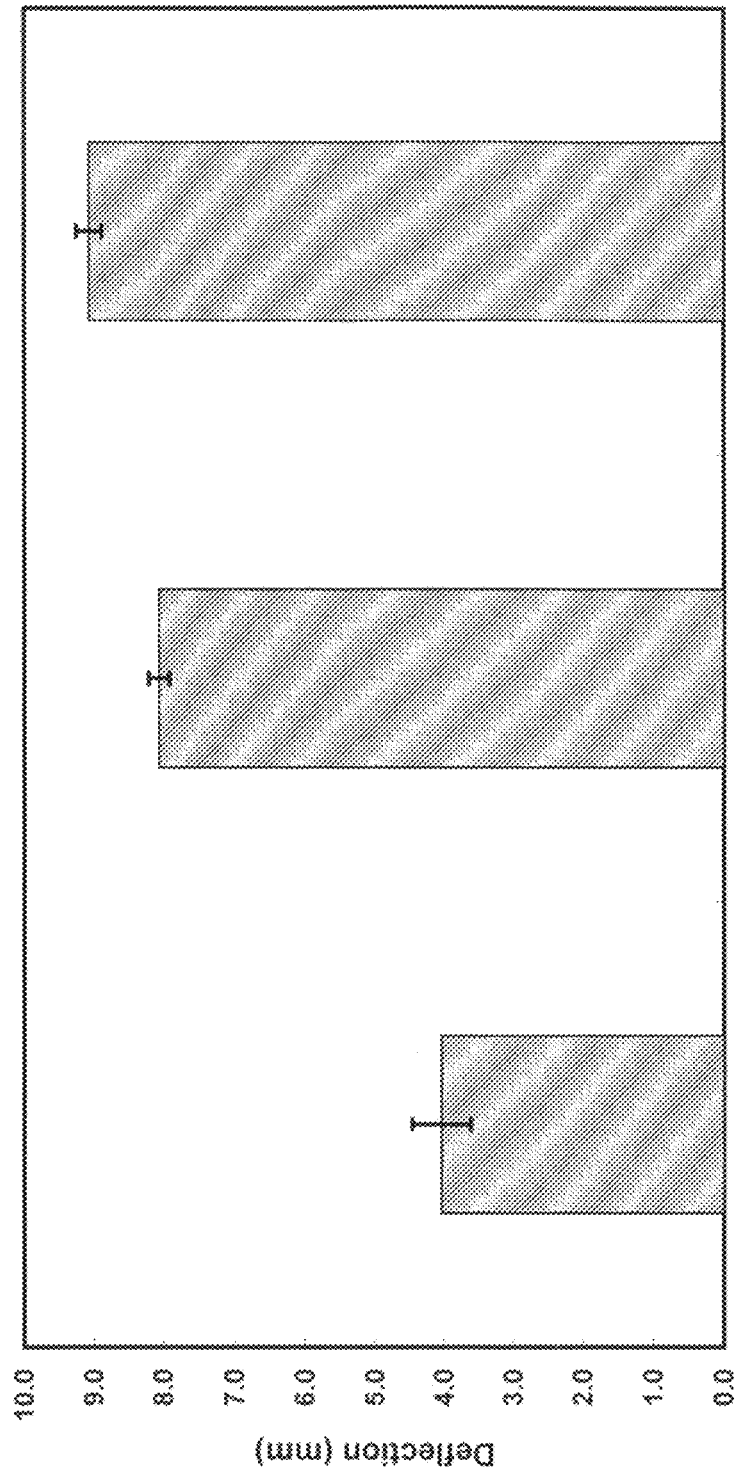
FIG. 4 is a graph showing the deflection (mm) during testing of the examples.
Figure 5:
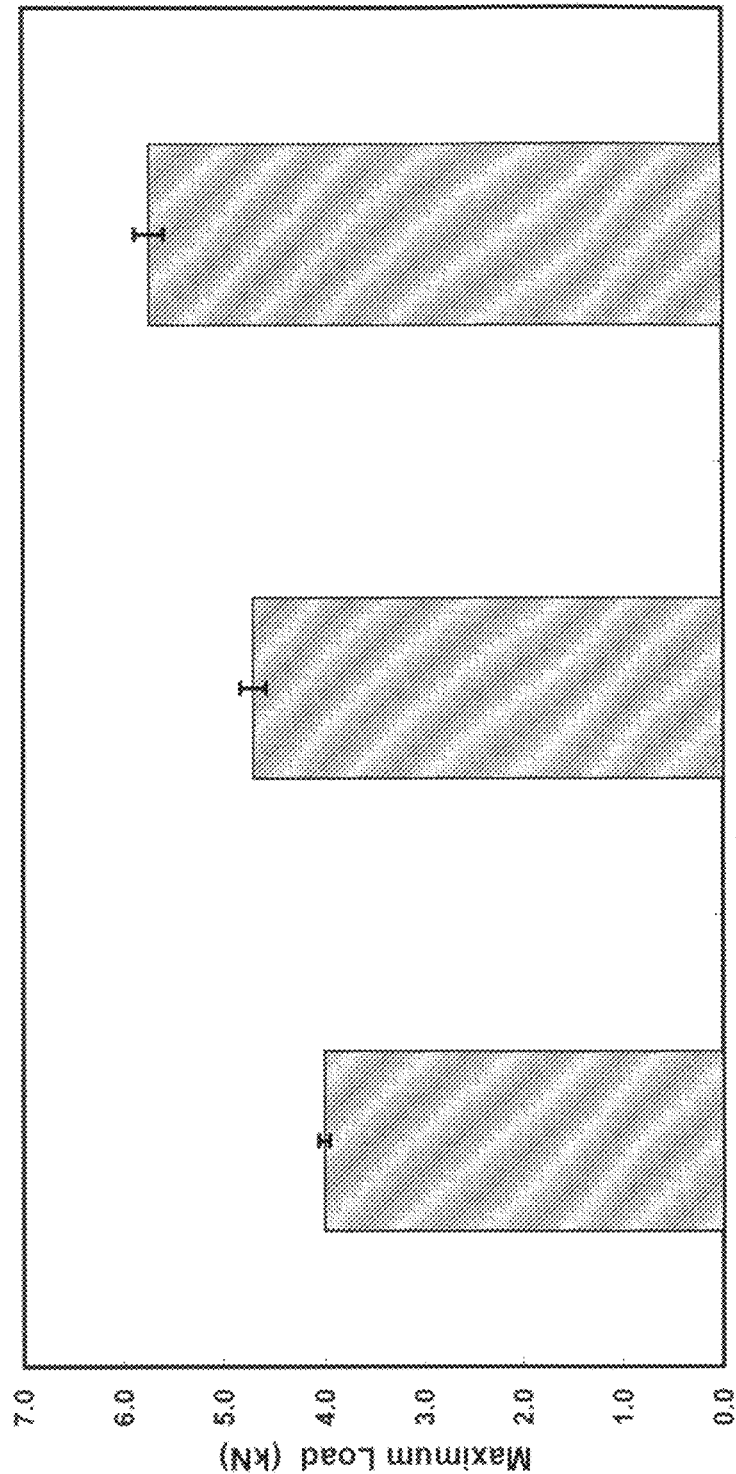
FIG. 5 is a graph showing the maximum load to penetration during testing of the examples.
Figure 6:
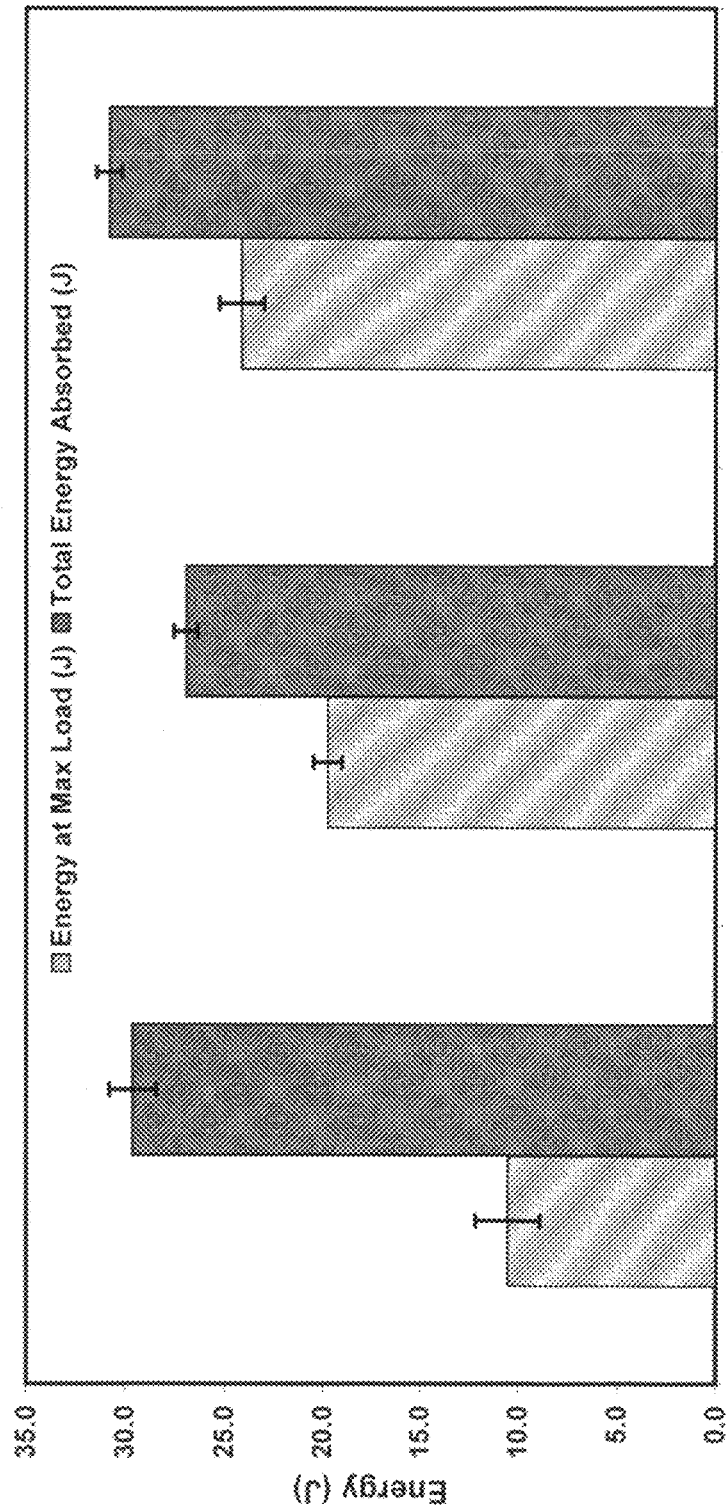
FIG. 6 is a graph showing the energy at maximum load and total energy absorbed during testing of the examples.

From a transverse loading perspective, an ideal tie layer is one that withstands the interlaminar shear stresses that develop between the layers of the fiber reinforced thermoplastic and thermoset structural element 10 during loading. These interlaminar stress values can be computed from knowledge of loading conditions, material properties, and structural properties. If the shear strength of the bond between the tie layer and the thermoplastic member and of the bond between the tie layer and the thermoset member and within the tie layer itself all exceed the shear stress levels that arise during loading up to and including failure, then the strength of the structure will be defined by failure through modes independent of the tie layer. The multiaxial impact test results are summarized in Table 3 and in FIGS. 4, 5, and 6.

TABLE 3

Testing data for examples

| ID | Failure Mode | Impact Velocity (m/s) | Total time (ms) | Deflection at Max Load (mm) | Impact Energy (J) | Max Load (kN) | Energy at Max Load (J) | Time to Max Load (ms) | Total Energy Absorbed (J) |
|---|---|---|---|---|---|---|---|---|---|
| Con. Ex. 1 | Brittle | 6.58 | 2.40 | 4.04 | 120.77 | 4.00 | 10.52 | 0.62 | 29.60 |
| Inv. Ex. 2 | Brittle | 6.58 | 2.30 | 8.06 | 120.78 | 4.70 | 19.74 | 1.26 | 26.93 |
| Inv. Ex. 3 | Brittle | 6.59 | 2.19 | 9.07 | 120.98 | 5.73 | 24.11 | 1.42 | 30.78 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A process for simultaneous consolidation of thermoplastic and thermoset members to form a fiber reinforced thermoplastic and thermoset element comprising:

a) providing a fiber reinforced thermoplastic member, wherein the fiber reinforced thermoplastic member comprises multiple layers of fibers and a thermoplastic matrix at least partially surrounding the fibers, wherein each layer of the fiber reinforced thermoplastic member is unconsolidated relative to one another, wherein the thermoplastic matrix comprises an "A" polymer and a "B" polymer, wherein the A polymer contains a polymer having at least 70% α-olefin units and is characterized by a melting temperature lower than the melting temperature of the exterior surface portion of the fibers, and the B polymer contains a co-polymer having at least 50% α-olefin units and is characterized by a number-average molecular weight of about 7,000 g/mol to 50,000 g/mol, a viscosity of between about 2,500 and 150,000 cP measured at 170° C., and a viscosity not greater than 10% of the viscosity of the A polymer measured at 170° C.;

b) providing a fiber reinforced thermoset member, wherein the fiber reinforced thermoset member comprises fibers and an uncured thermoset matrix at least partially surrounding the fibers;

c) applying a tie layer between the fiber reinforced thermoplastic member and the fiber reinforced thermoset member, wherein the tie layer comprises a first polymer and a second polymer, wherein the first polymer comprises a polyolefin, and wherein the second polymer comprises a polymer capable of chemically bonding with the thermoset polymer of the fiber reinforced thermoset member;

d) consolidating the fiber reinforced thermoplastic member, the tie layer, and the fiber reinforced thermoset member simultaneously under heat and optionally pressure to form the fiber reinforced thermoplastic and thermoset structural element, wherein after consolidation:

the thermoplastic matrix of the fiber reinforced thermoplastic member adheres at least a portion of the fibers of the fiber reinforced thermoplastic member together within each layer and between layers;

the thermoset matrix of the fiber reinforced thermoset member cures and adheres at least a portion of the fibers of the fiber reinforced thermoset member together;

the first polymer of the tie layer is mechanically bonded to the surface of the fiber reinforced thermoplastic member; and, the second polymer of the tie layer is chemically bonded to the surface of the fiber reinforced thermoset member.

2. The process of claim 1, wherein the tie layer is a multi-layered film comprising a first layer comprising the first polymer and a second layer comprising the second polymer.

3. The process of claim 1, wherein the tie layer is a monolayer comprising the first and second polymers.

4. The process of claim 1, wherein the thermoset matrix comprises an epoxy-based resin.

5. The process of claim 1, wherein the thermoset matrix comprises a phenolic polymer.

6. The process of claim 1, wherein the thermoset matrix comprises a vinyl-ester based resin.

7. The process of claim 1, wherein the fibers of the fiber reinforced thermoset member comprise carbon fibers.

8. The process of claim 1, wherein the fibers of the fiber reinforced thermoset member comprise glass fibers.

9. The process of claim 1, wherein the fibers of the fiber reinforced thermoset member comprise aramid fibers.

10. The process of claim 1, wherein the fibers of the fiber reinforced thermoplastic member comprise thermoplastic fibers.

11. The process of claim 1, wherein the fibers of the fiber reinforced thermoplastic member comprise glass fibers.

12. The process of claim 1, wherein the fibers of the fiber reinforced thermoplastic member comprise carbon fibers.

13. The process of claim 1, wherein the fibers of the fiber reinforced thermoplastic member comprise aramid fibers.

14. The process of claim 1, wherein consolidating the fiber reinforced thermoplastic member, the tie layer, and the fiber reinforced thermoset member simultaneously under heat and optionally pressure is performed in an autoclave.

15. The process of claim 1, wherein consolidating the fiber reinforced thermoplastic member, the tie layer, and the fiber reinforced thermoset member simultaneously under heat and optionally pressure is performed in an vacuum bag.

16. The process of claim 1, wherein consolidating the fiber reinforced thermoplastic member, the tie layer, and the fiber reinforced thermoset member simultaneously under heat and optionally pressure is performed at a pressure of between about 15-300 psi.

17. The process of claim 1, wherein the tie layer is a free standing film.

18. The process of claim 1, wherein the tie layer is applied to the fiber reinforced thermoplastic layer.

19. A process for simultaneous consolidation of thermoplastic and thermoset members to form a fiber reinforced thermoplastic and thermoset element comprising:

a) providing a fiber reinforced thermoplastic member, wherein the fiber reinforced thermoplastic member comprises multiple layers of fibers and a thermoplastic matrix at least partially surrounding the fibers, wherein each layer of the fiber reinforced thermoplastic member is unconsolidated relative to one another, wherein the thermoplastic matrix comprises an "A" polymer and a "B" polymer, wherein the A polymer contains a polymer having at least 70% α-olefin units and is characterized by a melting temperature lower than the melting temperature of the exterior surface portion of the fibers, and the B polymer contains a co-polymer having at least 50% α-olefin units and is characterized by a number-average molecular weight of about 7,000 g/mol to 50,000 g/mol, a viscosity of between about 2,500 and 150,000 cP measured at 170° C., and a viscosity not greater than 10% of the viscosity of the A polymer measured at 170° C.;

b) providing a fiber reinforced thermoset member, wherein the fiber reinforced thermoset member comprises fibers and an uncured thermoset matrix at least partially surrounding the fibers;

c) applying a tie layer between the fiber reinforced thermoplastic member and the fiber reinforced thermoset member, wherein the tie layer comprises a first polymer and a second polymer, wherein the first polymer comprises a polyolefin, and wherein the second polymer comprises a polymer capable of chemically bonding with the thermoset polymer of the fiber reinforced thermoset member, wherein the tie layer is discontinuous and wherein the tie layer is printed onto the fiber reinforced thermoplastic layer;

d) consolidating the fiber reinforced thermoplastic member, the tie layer, and the fiber reinforced thermoset member simultaneously under heat and optionally pressure to form the fiber reinforced thermoplastic and thermoset structural element, wherein after consolidation:

the thermoplastic matrix of the fiber reinforced thermoplastic member adheres at least a portion of the fibers of the fiber reinforced thermoplastic member together within each layer and between layers;

the thermoset matrix of the fiber reinforced thermoset member cures and adheres at least a portion of the fibers of the fiber reinforced thermoset member together;

the first polymer of the tie layer is mechanically bonded to the surface of the fiber reinforced thermoplastic member; and, the second polymer of the tie layer is chemically bonded to the surface of the fiber reinforced thermoset member.

20. The process of claim 1, wherein the first polymer of the tie layer comprises the same repeating unit as the thermoplastic matrix of the fiber reinforced thermoplastic member.

21. A process for simultaneous consolidation of thermoplastic and thermoset members to form a fiber reinforced thermoplastic and thermoset element comprising:

a) providing a fiber reinforced thermoplastic member, wherein the fiber reinforced thermoplastic member comprises multiple layers of fibers and a thermoplastic matrix at least partially surrounding the fibers, wherein each layer of the fiber reinforced thermoplastic member is unconsolidated relative to one another, wherein the thermoplastic matrix comprises an "A" polymer and a "B" polymer, wherein the A polymer contains a polymer having at least 70% α-olefin units and is characterized by a melting temperature lower than the melting temperature of the exterior surface portion of the fibers, and the B polymer contains a co-polymer having at least 50% α-olefin units and is characterized by a number-average molecular weight of about 7,000 g/mol to 50,000 g/mol, a viscosity of between about 2,500 and 150,000 cP measured at 170° C., and a viscosity not greater than 10% of the viscosity of the A polymer measured at 170° C.;

b) providing a fiber reinforced thermoset member, wherein the fiber reinforced thermoset member comprises fibers and an uncured thermoset matrix at least partially surrounding the fibers;

c) applying a tie layer between the fiber reinforced thermoplastic member and the fiber reinforced thermoset member, wherein the tie layer comprises a first polymer and a second polymer, wherein the first polymer comprises a polyolefin, and wherein the second polymer comprises a polymer capable of chemically bonding with the thermoset polymer of the fiber reinforced thermoset member, wherein the tie layer is discontinuous;

d) consolidating the fiber reinforced thermoplastic member, the tie layer, and the fiber reinforced thermoset member simultaneously under heat and optionally pressure to form the fiber reinforced thermoplastic and thermoset structural element, wherein after consolidation:

the thermoplastic matrix of the fiber reinforced thermoplastic member adheres at least a portion of the fibers of the fiber reinforced thermoplastic member together within each layer and between layers;

the thermoset matrix of the fiber reinforced thermoset member cures and adheres at least a portion of the fibers of the fiber reinforced thermoset member together;

the first polymer of the tie layer is mechanically bonded to the surface of the fiber reinforced thermoplastic member; and, the second polymer of the tie layer is chemically bonded to the surface of the fiber reinforced thermoset member.

* * * * *